United States Patent [19]
Ebel et al.

[11] Patent Number: 5,659,070
[45] Date of Patent: Aug. 19, 1997

[54] PREPARATION OF ALKYL 5-OXO-6-HEPTENOATES, AND NOVEL INTERMEDIATE FOR THE PREPARATION THEREOF

[75] Inventors: Klaus Ebel, Lampertheim; Matthias Eiermann, Limburgerhof; Thomas Papkalla, Mannheim, all of Germany

[73] Assignee: BASF Aktiengesellschaft, Ludwigshafen, Germany

[21] Appl. No.: 595,051

[22] Filed: Feb. 1, 1996

[30] Foreign Application Priority Data

Feb. 2, 1995 [DE] Germany ............ 195 03 327.2

[51] Int. Cl.$^6$ ............ C07C 69/738; C07C 69/73
[52] U.S. Cl. ............ 560/120; 560/174
[58] Field of Search ............ 560/120, 174

[56] References Cited

U.S. PATENT DOCUMENTS 2,806,047 9/1957 Bullock .

FOREIGN PATENT DOCUMENTS

| 634621 | 1/1962 | Canada . |
| 2016750 | 4/1970 | Germany . |
| 1096761 | 12/1967 | United Kingdom . |

OTHER PUBLICATIONS

Houben/Weyl, Methoden der organischen Chemie, vol. 7/2a, p. 445 1973.

*Primary Examiner*—Jose G. Dees
*Assistant Examiner*—Mary C. Cebulak
*Attorney, Agent, or Firm*—Keil & Weinkauf

[57] ABSTRACT

A process for preparing alkyl 5-oxo-6-heptenoates of the formula I

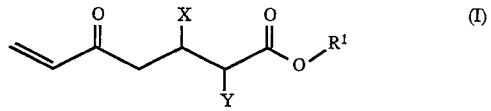

where X and Y are hydrogen or methyl, and $R^1$ is $C_1$–$C_8$-alkyl, by A) reacting 5-acetyl-2-norbornene with a dialkyl carbonate $[CO(OR^2)_2$, where $R^2$ is $C_1$–$C_4$-alkyl,] in the presence of a base to give an alkyl 3-(2-norbornen-5-yl)-3-oxopropionate II, B) reacting the ester II on the presence of a base with an unsaturated compound of the formula III

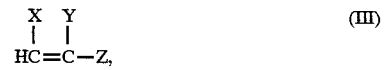

where Z is CN or $CO_2R^3$, where $R^3$ is $C_1$–$C_4$-alkyl, and hydrolyzing the product of the reaction of compound II with compound III to a 5-(2-norbornen-5-yl)-5-oxopentanoic acid of the formula IV, C) esterifying the acid IV to give a 5-(2-norbornen-5-yl)-5-oxopentanoic ester of the formula V, and D) converting the ester V by thermal cleavage into an alkyl 5-oxo-6-heptenoate I. The invention also relates to intermediates for preparing the esters I, to the use thereof and to an improved process for preparing alkyl 3-(2-norbornen-5-yl)-3-oxopropionates.

7 Claims, No Drawings

PREPARATION OF ALKYL 5-OXO-6-HEPTENOATES, AND NOVEL INTERMEDIATE FOR THE PREPARATION THEREOF

The present invention relates to a novel process for preparing alkyl 5-oxo-6-heptenoates of the general formula I

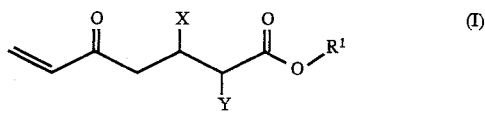

where X and Y are hydrogen or methyl, and $R^1$ is $C_1$–$C_8$-alkyl.

The invention furthermore relates to novel intermediates for preparing esters I, to the use thereof and to an improved process for preparing alkyl 3-(2-norbornen-5-yl)-3-oxopropionates.

Alkyl 5-oxo-6-heptenoates I are valuable compounds for preparing steroids (GB-A 1 096 761, DE-A 20 16 750).

The corresponding methyl ester can be obtained by reacting glutaryl chloride, 2 equivalents of aluminum chloride and ethylene to give methyl 7-chloro-5-oxoheptanoate, followed by elimination of hydrogen chloride (Houben-Weyl, Methoden der Organischen Chemie, Vol. 2/7a, page 445). However, glutaric acid compounds are available only in small quantities on the industrial scale.

It is an object of the present invention to find a process for preparing alkyl 5-oxo-6-heptenoates I which avoids the use of glutaric acid derivatives. A further object was, because of the tendency of the products I to polymerize, to find storage-stable compounds from which the esters I can be liberated as required.

We have found that this object is achieved by a process for preparing the esters I, which comprises A) reacting 5-acetyl-2-norbornene with a dialkyl carbonate $CO(OR^2)_2$, where $R^2$ is $C_1$–$C_4$-alkyl, in the presence of a base to give an alkyl 3-(2-norbornen-5-yl)-3-oxopropionate of the formula II

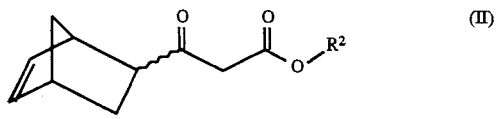

B) reacting the ester II in the presence of a base with an unsaturated compound of the formula III $$\begin{array}{c} X\ \ Y \\ |\ \ | \\ HC=C-Z, \end{array}$$ (III)

where Z is CN or $CO_2R^3$, where $R^3$ is $C_1$–$C_4$-alkyl, and hydrolyzing to a 5-(2-norbornen-5-yl)-5-oxopentanoic acid of the formula IV

C) esterifying the acid IV to give a 5-(2-norbornen-5-yl)-5-oxopentanoic ester of the formula V

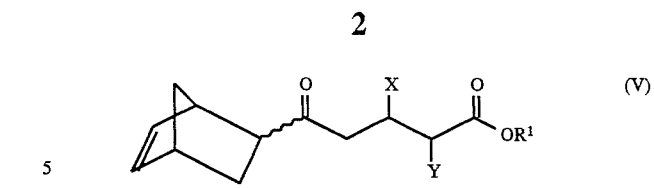

D) and converting the latter by thermal cleavage at from 300° to 700° C. into an alkyl 5-oxo-6-heptenoate I.

We have furthermore found novel compounds of the formulae IV and V which are storage-stable precursors for the compounds I.

We have additionally found an improved process for preparing alkyl 3-(2-norbornen-5-yl)-3-oxopropionates of the formula II, which themselves are intermediates in the process for the preparing the esters I.

Process Step A

5-Acetyl-2-norbornene can be used as mixture of the exo and endo forms. This compound is preferably prepared from methyl vinyl ketone and cyclopentadiene by Diels-Alder reaction (eg. Dinwiddie et al., J. Org. Chem. 30 (1965) 766). However, preparation from dicyclopentadiene is also suitable (eg. DE-A 16 18 145).

5-Acetyl-2-norbornene is reacted with a di-($C_1$–$C_4$-alkyl) carbonate, preferably with dimethyl carbonate, and a base, eg. an alkali metal alcoholate such as sodium methanolate, sodium ethanolate and potassium methanolate, an alkali metal amide such as sodamide, but preferably an alkali metal hydride, especially sodium hydride, to give an alkyl 3-(2-norbornen-5-yl)-3-oxopropionate II.

The reaction has been disclosed (cf. Stork et al., Tetrahedron Lett. (1972) 2755), but it is difficult to control the reaction when all the components are heated in an inert solvent because of the amount of heat liberated, and the space-time yield is unsatisfactory. These disadvantages also apply to a variant (Caselli et al., Austr. J. Chem. 35 (1982) 799) in which 5-acetyl-2-norbornene is added to a mixture of the base and the dialkyl carbonate.

An embodiment in which 5-acetyl-2-norbornene is added, mixed with dialkyl carbonate, to the base is therefore preferred.

The base is, as a rule, used in stoichiometric quantity, ie. normally 2 equivalents per equivalent of 5-acetyl-2-norbornene, but it can also be used in excess. The dialkyl carbonate is also generally used in an excess of from 2 to 6 equivalents per equivalent of 5-acetyl-2-norbornene.

The use of an inert solvent, eg. an ether such as 1,2-dimethoxyethane, is possible, but it is more advantageous to carry out the reaction in an excess of dialkyl carbonate which simultaneously acts as solvent.

After the components have been mixed, the mixture is heated at, for example, 30° to 70° C. until the reaction is complete. The reaction typically takes from 5 to 20 h.

The 3-oxopropionic ester II is advantageously isolated by hydrolyzing the reaction mixture, extracting the product with an organic solvent such as toluene, and working up by distillation.

Process Step B

The ester II—in the exo form, the endo form or as mixture—can be added onto an unsaturated compound III. The latter is, specific-ally acrylonitrile, methyl acrylate, ethyl acrylate, propyl acrylate, n-butyl acrylate and the corresponding methacrylic esters and 2-butenecarboxylic esters.

The ester II and the unsaturated compound III are used in equimolar amounts as a rule.

The reaction is carried out in the presence of catalytic amounts of a base, eg. an alkali metal alcoholate or hydroxide, preferably sodium methoxide. The reaction can be carried out in a solvent, but a reaction without solvent is preferred. The unsaturated compound III is advantageously added to a mixture of the ester II and the base.

After reaction at, in general, from 20° to 80° C. for, for example, 2 to 20 h, the mixture is hydrolyzed in situ to 5-(2-norbornen-5-yl)-5-oxopentanoic acid.

The hydrolysis is carried out in a conventional way, for example by adding a base such as sodium hydroxide to the reaction mixture, and heating for several hours.

The acids IV can be isolated by extraction.

Process Step C

The acid IV can be converted into an ester V carrying $C_1$–$C_8$-alkyl radicals by esterification by conventional methods (see Houben-Weyl, Methoden der Organischen Chemie, Volume E5). The methyl and ethyl esters are preferred. It is particularly advantageous to use catalytic amounts of an acid, eg. mineral acids such as sulfuric acid or sulfonic acids such as p-toluenesulfonic acid and $C_1$–$C_8$-dialkyl ketals such as 2,2-dimethoxypropane or a $C_1$–$C_8$-trialkyl orthoester such as trimethyl orthoformate.

The products V can be isolated by neutralizing the reaction mixture with an aqueous base, extracting with an organic solvent and distilling. The esters V are compounds stable on storage at room temperature which show no noticeable signs of undesired polymerization even after months.

Process Step D

The esters V can be thermally cleaved to cyclopentadiene and the products I. Temperatures from 300° to 700° C. are required for this retro-Diels-Alder reaction, and 450°–600° C. is preferred. The reaction is carried out in the gas phase. The pressure during this step is generally from 0.01 to 10 mbar, preferably 1 to 2 mbar. The resulting crude product is preferably worked up by distillation to give the products I.

The novel process for preparing alkyl 5-oxo-6-heptenoates I can be carried out without using glutaric acid derivatives. It gives the required products in good yields. The intermediates formed therein, the 5-(2-norbornen-5-yl)-5-oxopentanoic acids IV and, in particular, the corresponding alkyl esters V, are forms of the esters I which can be handled conveniently and are stable on storage at room temperature.

EXAMPLES

Process Step A

Example 1

Preparation of methyl exo/endo-3-(2-norbornen-5-yl)-3-oxopropionate 66.7 g of 60% sodium hydride in white oil were mixed with 200 ml of anhydrous 1,2-dimethoxyethane and, while refluxing under nitrogen, a mixture of 644 g of dimethyl carbonate and 108.8 g of exo/endo-5-acetyl-2-norbornene was added dropwise, and the mixture was then boiled for 16–20 h. After cooling, the mixture was poured into ice/sodium bicarbonate, neutralized with 10% strength hydrochloric acid and extracted twice with 200 ml of toluene each time. The collected organic phases were washed with water, dried with magnesium sulfate and distilled under reduced pressure.

Boiling point 85°–90° C./0.5 mbar, yield 113.9 g (73%).

Example 2

Preparation of ethyl exo/endo-3-(2-norbornen-5-yl)-3-oxopropionate 160 g of sodium ethoxide were mixed with 350 ml of anhydrous 1,2-dimethoxyethane and, while refluxing under nitrogen, a mixture of 1.06 kg of diethyl carbonate and 136 g of exo/endo-5-acetyl-2-norbornene was added dropwise, and the mixture was then boiled for 16–20 h. Working up took place as in Example 1.

Boiling point 94°–111° C./0.5 mbar, yield 75 g (36%).

Process Step B

Example 3

Preparation of exo/endo-5-(2-norbornen-5-yl)-5-oxopentanoic acid 58.0 g of methyl acrylate were added under nitrogen at 40° C. to 2.0 g of sodium methoxide and 130.4 g of methyl exo/endo-3-(2-norbornen-5-yl)-3-oxopropionate. After 16 h at 40° C., 550 ml of 5N aqueous sodium hydroxide solution were added, and the mixture was boiled for 2 h. After cooling it was extracted twice with 200 ml of ether each time. Small amounts of exo/endo-5-acetyl-2-norbornene could be isolated from the ether phases. The aqueous phase was adjusted to pH 1 with concentrated hydrochloric acid and extracted three times with 100 ml of ether each time. The combined organic extracts were washed with 100 ml of 5% strength aqueous hydrochloric acid, dried with magnesium sulfate and concentrated. Crude yield (exo/endo≈1:1) 128.0 g.

$^1$H-NMR(CDCl$_3$): 1.2–1.6 (m, 6H); 1.7–2.0 (m, 6H); 2.3–2.7 (m, 9H); 2.95 (br.s, 2H); 2.98 (br.s, 1H); 3.00 (m, 1H); 3.20 (br.s, 1H); 5.80 (m, 1H, —CH=); 6.18 (m, 3H, —CH=); 8.6 (br., —COOH).

$^{13}$C-NMR (CDCl$_3$): 18.61; 18.75; 27.46; 29.22; 33.07; 33.11; 40.41; 41.28; 41.68; 42.67; 45.53; 45.90; 46.03; 49.96; 50.80; 51.65; 131.16; 135.83; 137.92; 138.40; 179.33; 179.36; 210.48; 212.26.

Example 4

Preparation of exo/endo-5-(2-norbornen-5-yl)-5-oxopentanoic acid

The reaction took place as in Example 3 but with the methyl acrylate being replaced by 35.7 g of acrylonitrile. The reaction time with the 5N aqueous sodium hydroxide solution was extended to 48 h.

Process Step C

Example 5

Preparation of methyl exo/endo-5-(2-norbornen-5-yl)-5-oxopentanoate 128 g of the crude yield from Example 3 were boiled with 73.8 g of 2,2-dimethoxypropane and 12.3 g of p-toluenesulfonic acid in 290 ml of methanol for 3 h. The mixture was cooled and concentrated, and then made alkaline with 2N aqueous sodium hydroxide solution and extracted twice with 200 ml of ether each time. The combined ether phases were washed with 100 ml of water, dried with magnesium sulfate and distilled. Distillate (exo/endo≈1:1, boiling point 115°–120° C./1 mbar) 69 g (46% yield over Examples 3 and 5).

$^1$H-NMR (CDCl$_3$): 1.2–1.6 (m, 6H); 1.7–2.0 (m, 6H); 2.3–2.4 (m, 5H); 2.5–2.7 (m, 4H); 2.90 (br.s, 2H); 2.95 (br.s, 1H); 3.00 (m, 1H); 3.25 (br.s, 1H); 3.65 (s, 6H, —OCH$_3$); 5.80 (m, 1H, —CH=); 6.15 (m, 3H, —CH=).

$^{13}$C-NMR (CDCl$_3$): 18.94; 19.07; 27.37; 29.16; 33.00; 33.04; 40.42; 41.32; 41.70; 42.69; 45.63; 45.85; 45.98; 49.94; 50.67; 51.41; 51.54; 131.28; 135.87; 137.69; 138.17; 173.48; 209.65; 211.54.

IR (KBr): 1702; 1735 cm$^{-1}$.

Example 6

Preparation of methyl exo/endo-5-(2-norbornen-5-yl)-5-oxopentanoate 8.5 g of the crude yield from Example 3 were boiled with 2 ml of methanol, 0.2 ml of concentrated hydrochloric acid and 0.9 g of anhydrous calcium chloride for 30 minutes. The phases were separated, and after adding sodium bicarbonate to the aqueous phase it was extracted with 10 ml of toluene. The combined organic phases were dried with magnesium sulfate and distilled. Distillate iexo/endo≈1:1) 4.5 g (46% yield over Examples 3 and 6).

Process Step D

Example 7

Preparation of methyl 5-oxo-6-heptenoate 29.9 g of methyl exo/endo-5-(2-norbornen-5-yl)-5-oxopentanoate were added to the top of a vertical quartz glass tube reactor (length 30 cm×diameter 3 cm), which was packed with quartz glass rings (length 10 mm×diameter 4 mm), under a pressure of 1 mbar and at 538° to 548° C. over the course of 3 h. The product was taken up from the lower end of the reactor and condensed (crude yield 19.2 g) and subsequently distilled under 1 mbar. Distillate 15.8 g (75%).

We claim:

1. A process for preparing alkyl 5-oxo-6-heptenoates of the general formula I

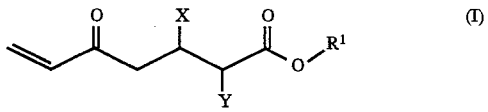

where X and Y are hydrogen or methyl, and R$^1$ is C$_1$–C$_8$-alkyl, which comprises A) reacting 5-acetyl-2-norbornene with a dialkyl carbonate CO(OR$^2$)$_2$, where R$^2$ is C$_1$–C$_4$-alkyl, in the presence of a base to give an alkyl 3-(2-norbornen-5-yl)-3-oxopropionate of the formula II

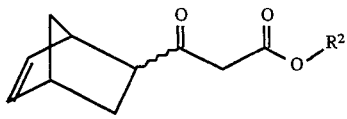

B) reacting the ester II in the presence of a base with an unsaturated compound of the formula III

where Z is CN or CO$_2$R$^3$, where R$^3$ is C$_1$–C$_4$-alkyl, and hydrolyzing to a 5-(2-norbornen-5-yl)-5-oxopentanoic acid of the formula IV

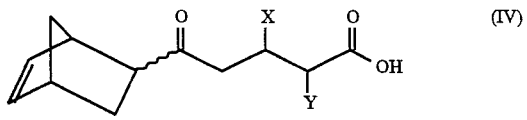

C) esterifying the acid IV with the alcohol R'OH to give a 5-(2-norbornen-5-yl)-5-oxopentanoic ester of the formula V

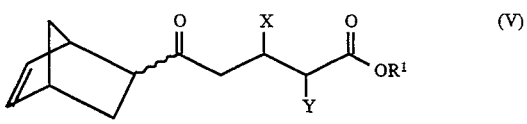

D) and converting the latter by thermal cleavage at from 300° to 700° C. into an alkyl 5-oxo-6-heptenoate I.

2. A process as defined in claim 1, wherein 5-acetyl-2-norbornene is prepared from methyl vinyl ketone and cyclopentadiene.

3. A process as defined in claim 1, wherein methyl 5-oxo-6-heptenoate is prepared.

4. A process as defined in claim 1, wherein the esterification in step C) is carried out in the presence of catalytic amounts of an acid with a C$_1$–C$_8$-dialkyl ketal or a C$_1$–C$_8$-trialkyl orthoester.

5. A 1,4-keto carboxylic acid derivative of the formula IV or V

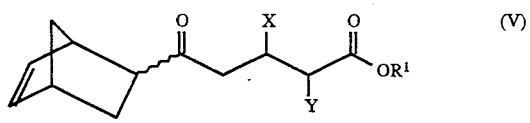

where X and Y are hydrogen or methyl, and R$^1$ is C$_1$–C$_8$-alkyl.

6. A process for preparing alkyl 3-(2-norbornen-5-yl)-3-oxopropionates of the formula II by reacting 5-acetyl-2-norbornene with a dialkyl carbonate and a base, wherein 5-acetyl-2-norbornene is added in a mixture with the dialkyl carbonate to the base.

7. A process as defined in claim 1, wherein the process in stage A) comprises reacting 5-acetyl-2-norbornene with a dialkyl carbonate and a base, wherein 5-acetyl-2-norbornene is added in a mixture with the dialkyl carbonate to the base.

* * * * *